(12) United States Patent
Sugiyama et al.

(10) Patent No.: US 7,507,567 B2
(45) Date of Patent: Mar. 24, 2009

(54) RNA POLYMERASE MUTANTS WITH INCREASED THERMOSTABILITY

(75) Inventors: Akio Sugiyama, Tsuruga (JP); Yoshiaki Nishiya, Tsuruga (JP); Bunsei Kawakami, Fukui-Ken (JP)

(73) Assignee: bioMerieus B.V., Boxtel (NL)

( * ) Notice: Subject to any disclaimer, the term of this patent is extended or adjusted under 35 U.S.C. 154(b) by 372 days.

(21) Appl. No.: 10/220,908

(22) PCT Filed: Mar. 1, 2001

(86) PCT No.: PCT/EP01/02327

§ 371 (c)(1), (2), (4) Date: Feb. 11, 2003

(87) PCT Pub. No.: WO01/66705

PCT Pub. Date: Sep. 13, 2001

(65) Prior Publication Data

US 2003/0175738 A1 Sep. 18, 2003

(30) Foreign Application Priority Data

Mar. 7, 2000 (EP) .................... 00200787

(51) Int. Cl.
- *C12N 9/12* (2006.01)
- *C12N 15/11* (2006.01)
- *C12N 1/20* (2006.01)
- *C12P 19/34* (2006.01)

(52) U.S. Cl. ............... 435/194; 435/183; 435/320.1; 435/252.3; 435/91.1; 536/23.1; 536/23.2

(58) Field of Classification Search .......... 435/194, 435/183, 410, 320.1, 252.3, 69.1; 538/231, 538/232; 530/350
See application file for complete search history.

(56) References Cited

U.S. PATENT DOCUMENTS

| 4,952,496 A | 8/1990 | Studier et al. |
| 5,385,834 A | 1/1995 | Ikeda |

FOREIGN PATENT DOCUMENTS

| EP | 0 329 822 | 8/1989 |
| EP | 0 939 130 A1 | 9/1999 |
| FR | 2 761 695 | 10/1998 |
| WO | WO 00/36112 | 6/2000 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

Gardner et al., "Initiation, Elongation, and Processivity of Carboxyl-Terminal Mutants of T7 RNA Polymerase," *Biochemistry* 36 2908-2918 (1997).

* cited by examiner

*Primary Examiner*—Richard G Hutson
(74) *Attorney, Agent, or Firm*—Meyers Bigel Sibley & Sajovec, P.A.

(57) ABSTRACT

The present application relates to mutated RNA polymerases from bacteriophages that have increased stability, for example under high temperature conditions. Preferred mutated RNA polymerases according to the invention are mutant RNA polymerases from T7 or SP3 bacteriophages. An especially preferred embodiment of the present invention is a T7 RNA polymerase with a serine to proline amino acid change in the protein at position 633 of the amino acid sequence.

22 Claims, 1 Drawing Sheet

T7 RNAP　　　Thermo-T7 RNAP
Reaction Temp:　37 45 48 51　M　37 45 48 51

-Template plasmid
- Transcribed RNA

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 1
gtgtgactaa gcgtccggtc atgacgctgg                                    30

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2
ccagcgtcat gaccggacgc ttagtcacac                                    30

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3
gtttacgctg tcccaatgtt caacccgcaa                                    30

<210> SEQ ID NO 4
<211> LENGTH: 30
<212> TYPE: DNA
<213> ORGANISM: Artificial sequence
<220> FEATURE:
<223> OTHER INFORMATION: Synthetic oligonulceotide

<400> SEQUENCE: 4
ttgcgggttg aacattggca cagcgtaaac                                    30

<210> SEQ ID NO 5
<211> LENGTH: 30
<212> TYPE: DNA
<213> ORGANISM: Artificial sequence
<220> FEATURE:
<223> OTHER INFORMATION: Synthetic oligonulceotide

<400> SEQUENCE: 5
```

```
ttctacgacc agatcgctga ccagttgcac                               30

<210> SEQ ID NO 6
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 6
gtgcaactgg tcagcgatct ggtcgtagaa                               30

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
tcttagagtc ggactacgcg ttcgcgtaac                               30

<210> SEQ ID NO 8
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 8
gttacgcgaa cgcgtagtcc gactctaaga                               30
```

RNA POLYMERASE MUTANTS WITH INCREASED THERMOSTABILITY

The present application relates to mutated RNA polymerases from bacteriophages that have increased stability, for example under high temperature conditions. One example of bacteriophage encoded RNA polymerase is the T7 RNA polymerase. T7 is a bacteriophage capable of infecting *E. coli* cells. Examples of other *E. coli* infecting T7-like bacteriophages are T3, φI, φII, W31, H, Y, A1, croC21, C22 and C23. An example of a *Salmonella typhimurium* infecting bacteriophage is SP6.

The RNA polymerases of bacteriophages have high selectivity for their own promoter sequence. The T7 RNA polymerase will bind the T7 RNA polymerase promoter sequence but not one of the other bacteriophage promoter sequences. The high promoter specificity ensures that the bacteriophage transcription reaction is only directed to its own genome and not the host genome. The entire nucleotide sequence of the T7 bacteriophage is known and the phage RNA polymerase is encoded by T7 gene 1. Other RNA polymerases that resemble the T7 RNA polymerase are the RNA polymerases of bacteriophages SP6 and T3. The T3 RNAP shows about 80% homology with the T7 RNAP.

The T7 gene 1 has been cloned and expressed in bacteria allowing the production of large quantities of the enzyme (Studier et al., U.S. Pat. No. 4,952,496). The T7 polymerase is a single chain protein of 883 amino acids with a molecular weight of 98,6 Kda. T7 RNA polymerase does not require any auxiliary factors for accurate transcription. The enzyme alone is capable of recognizing it's promoters, initiating transcription, elongating the RNA transcript and terminating transcription. T7 RNA polymerase is very efficient in transcribing DNA from its own promoters and elongates RNA five times faster compared to *E. coli* RNA polymerase. Their selectivity, activity and ability to produce complete transcripts make the polymerases from bacteriophages very useful for a variety of purposes.

The present invention is concerned with the RNA polymerases of T7-like bacteriophages that have been mutated.

Some specific mutants of T7-like bacteriophage RNA polymerases have been described. For example, in WO91/05866 an alternative expression system is described. The system is an attempt to use the bacteriophage T7 promoters to direct the transcription of a cloned gene in bacteria. The system uses a truncated T7 RNA polymerase, the gene of which is mutated by deleting a nucleotide (one or more bases corresponding to base 3809 and 3877 of a wild type T7 polymerase gene). This deletion results in a frame shift and consequently a new translation stop codon is created. In U.S. Pat. No. 5,385,834, a mutant T7 RNAP is also described. The mutant described in U.S. Pat. No. 5,385,834 is a G to A transition at nucleotide 664 of T7 gene 1 that converts glutamic acid (222) to lysine. This mutant exhibit altered promoter recognition, and thus the mutant is able to initiate transcription from T7 promoter point mutations that are normally inactive.

Ikeda et al. (Ikeda, R. A. et al. Biochemistry, 31:9073-9080, 1992 and Ikeda, R. A. et al., Nucl. Acid. Res., 20: 2517-2524, 1992) have described two compatible plasmids that can be used for screening the activity of mutated T7 RNAP gene- or promoter sequences. The first plasmid carries the T7 gene 1 (the gene encoding the T7 RNA polymerase) ligated to an *E. coli* tac promoter, while the second plasmid carries the gene encoding CAT (chloramphenicol acetyl transferase) ligated to the T7 promoter. *E. coli* cells carrying these two plasmids are CAM (chloramphenicol) resistant if the T7 polymerase interacts with the T7 promoter and transcribes the CAT gene from the second plasmid. If either the T7 promoter or the T7 RNA polymerase is inactive, the CAT gene will not be transcribed and thus the *E. coli* cells will be cam sensitive. Ikeda et al. used the plasmids to investigate the effects of certain mutations on the activity of T7 RNA polymerase promoters. With a plasmid system like the one described by Ikeda et al., where the T7 RNA polymerase gene 1 is on one plasmid under the control of a suitable promoter, and the T7 RNA polymerase promoter is on a second plasmid controlling a resistance gene like CAT, mutant T7 RNA polymerases itself can be screened for their activity as well.

In vitro transcription with the aid of bacteriophage encoded RNA polymerases (e.g. T7 RNA polymerase, T3 RNA polymerase, and SP6 RNA polymerase) has become a widely applied tool in molecular biology. Next to the in vitro transcription on its own, as a tool to make fast amounts of RNA bacteriophage, RNA polymerases are part of nucleic acid amplification methods. Such methods are for instance NASBA, 3SR and TMA. In vitro transcription has also been described in combination with PCR as an extra linear amplification step post PCR amplification.

For all of the above applications it would be advantageous if the reaction temperature could be elevated so that the kinetics of the transcription reaction becomes better and more importantly that isothermal amplification methods (NASBA, 3SR and TMA) can be performed at higher temperatures. This higher incubation temperature of the isothermal amplification reaction will enable the amplification of structured RNA's more efficiently. Applications where this is important are amplification of long RNA sequences (>500 nucleotides) and multiplex reactions (i.e. the amplification of multiple RNA sequences in one reaction mixture).

The present invention relates to mutants of T7 like bacteriophage derived RNA polymerases that have an increased stability.

Analysis of randomly mutated T7 RNA polymerase mutants revealed a number of possible mutations that have a stabilizing effect on the T7 RNA polymerase protein and enable enzymatic activity at higher temperatures than normal (normal is 37° C.-41° C.). The randomly mutated T7 RNA polymerase sequences were analyzed by screening the sequences in a two plasmid system as described by Ikeda et al (1992) in *Bacillus stearothermophilus*. The *Bacillus stearothermophilus* cells were grown at elevated temperatures (45°-50° C.) and CAM resistance could only be obtained if a mutated T7 sequence would encode a more stable T7 RNA polymerase capable of polymerase activity at these temperatures. In the *Bacillus stearothermophilus* system one plasmid contains an antibiotic resistance gene (CAT) under control of the T7 promoter and the other plasmid contains a mutant library of the T7 RNA polymerase under control of a Bacillus promoter. In those cases where the mutation allows the T7 RNA polymerase to be functional at the elevated temperature the *Bacillus stearothermophilus* will have become CAM resistant.

Mutants of the T7 polymerase that have an increased stability have already been described in co-pending, co-owned application number PCT/EP99/09716, the contents of which are herewith incorporated by reference.

One of the mutations described in PCT/EP99/09716 was a mutation from Serine to Proline at position 633 of the enzyme.

With the present invention yet further mutations have been found that also increase the stability of the enzyme.

Mutations according to the invention include an F849I, an F880Y and an S430P mutation in the T7 sequence.

Preferred are those mutants that comprise more than one of these mutations, preferably in combination with the S633P mutation. Mutants according to the invention may, for example, comprise the S633P mutation in combination with either the F849I mutation or the F880Y mutation. Another mutant according to the invention comprises the F84I mutation in combination with the F880Y mutation.

Good results with regard to the improved stability were also obtained with a mutant comprising the S633P mutation and the F849I mutation as well as the F880Y mutation. The most preferred embodiment of the present invention is a quadruple mutant (mutant comprising 4 mutations) comprising the S430P, the S633P, the F849I and the F880Y mutation.

This mutant is at least 44 times more thermostable than the wild type enzyme at 50° C. (having a T ½ of 84.5 minutes vs. 1.9 minutes for the wild type)! Furthermore the specific activity of the quadruple mutant at 50° C. is about 12 times as high as that of the wild type enzyme at 50° C. (56.8 units/µg for the mutant vs. 4.8 units/µg for the wild type).

Preferred mutated RNA polymerases according to the invention are mutant RNA polymerases from T7 or SP3 bacteriophages. Due to the high homology between these enzymes, mutations in the T7 gene 1 sequence are likely to have the same effect in the corresponding gene sequence of the T3 bacteriophage. Since there is 80% homology between the T7 RNA polymerase and the T3 RNA polymerase the same effects of the 633 serine→proline mutation in the T7 gene may be expected for a 634 serine→proline amino acid mutation in the T3 RNA polymerase.

A gene encoding an RNA polymerase, said gene containing one or more mutations resulting in an increased stability of the encoded RNA polymerase, when compared with the wild type protein is likewise part of the present invention, especially where the T7 or T3 RNA polymerase encoding genes are concerned.

A serine to proline amino acid change in the protein at position 633 of the amino acid sequence of the T7 RNA polymerase is the result of a T→C mutation at position 1897 of the T7 RNA polymerase nucleotide sequence.

The mutations are scored compared to the T7 RNA polymerase wild-type sequence (SEQ ID NOS: 9 and 10)as published by Dunn, J. J. and Studier, F. W. [(1983) Complete nucleotide sequence of bacteriophage T7 DNA and the locations of T7 genetic elements *J. Mol. Biol.* 166 (4), 477-535] with number one being the first nucleotide of the T7 RNA polymerase gene, which is nucleotide number 3171 in the complete genome sequence of bacteriophage T7.

The present invention further relates to expression vehicles for the expression of the mutated RNA polymerases according to the invention.

In order to express a gene, the gene is brought under the control of regulating sequences enabling expression of the protein encoded by said gene. Usually, this is done by cloning the gene to be expressed downstream of such regulating sequences. Regulating sequences enabling expression of genes or fragments of genes may e.g. be promoter-sequences either or not in combination with enhancer sequences.

These sequences may be the promoter sequences that are found to be linked to the gene in its native form. Alternatively it may be heterologous promoters. An advantage of using heterologous promoters is that they offer the possibility to express the gene in host cells that do not recognize the gene's native promoter. Moreover, the heterologous promoter may be a promoter that is inducible, so that expression of the gene can be started at any desired moment.

Promoter sites are sequences to which RNA polymerase binds, initial to transcription. Promoter-sites exist in a variety of types, i.a. depending on the type of cell, they originate from. Promoter sequences have been described for promoters from prokaryotic, eukaryotic, and viral origin. Recombinant DNA molecules of the above mentioned type can e.g. be made by cutting a suitable DNA fragment with a suitable restriction enzyme, cutting a fragment containing regulating sequences with the same enzyme and ligating both fragments in such a way, that the nucleic acid sequence to be expressed is under the control of the promoter sequence. Many variant approaches to make useful recombinants have been described in Sambrook (Sambrook et al, Molecular cloning, a laboratory manual. Cold Spring Laboratory Press, Cold Spring Harbor, N.Y. (1989)).

In general, recombinant nucleic acid sequences will be cloned into a so-called vector molecule. The then formed recombinant vector molecule, often capable of self-replication in a suitable host cell, can be used to bring the cloned nucleic acid sequences into a cell. This may be a cell in which replication of the recombinant vector molecule occurs. It may also be a cell in which a regulating sequence of the vector is recognised, so that a mutated RNA polymerase according to the present invention is expressed. A wide range of vectors is currently known, including vectors for use in bacteria, e.g. pBR322, 325 and 328, various pUC-vectors i.a. pUC 8, 9, 18, 19, specific expression-vectors; pGEM, pGEX, and Bluescript[(R)], vectors based on bacteriophages; lambda-gtwes, Charon 28, M13-derived phages, vectors for expression in eukaryotic cells containing viral sequences on the basis of SV40, papilloma-virus, adenovirus or polyomavirus (Rodriquez, R. L. and Denhardt, D. T., ed.; Vectors: A survey of molecular cloning vectors and their uses, Butterworths (1988), Lenstra et al, Arch. Virol.; 110: 1-24 (1990)). All recombinant molecules comprising the nucleic acid sequence under the control of regulating sequences enabling expression of the mutated RNA polymerase are considered to be part of the present invention.

Furthermore the invention comprises a host cell containing a nucleic acid sequence encoding the mutated RNA polymerase, or a recombinant nucleic acid molecule encoding the mutated RNA polymerase under the control of regulating sequences enabling expression of the mutated RNA polymerase.

The invention also comprises a host cell containing a virus vector containing a nucleic acid molecule encoding the mutated RNA polymerase, or a recombinant nucleic acid molecule encoding the mutated RNA polymerase under the control of regulating sequences enabling expression of the mutated RNA polymerase.

Frequently used expression systems are bacterial, yeast, fungal, insect and mammalian cell expression systems. Such systems are well-known in the art and easily available, e.g. commercially trough Clontech Laboratories, Inc. 4030 Fabian Way, Palo Alto, Calif. 94303-4607, USA A host cell may be a cell of bacterial origin, e.g. *Escherichia coli*, *Bacillus subtilis* and *Lactobacillus* species, in combination with bacteria-based vectors as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Thus, an expression vector comprising a gene encoding an RNA polymerase according to the invention and suitable expression control sequences is likewise part of the present invention, as well as the host cells transformed therewith.

The mutated RNA polymerases according to the invention will find their use in all processes where RNA polymerases are normally used and where the RNA polymerases, for example, would be used at elevated temperatures and thus an improved stability would be advantageous.

The mutated RNA polymerases according to the invention would be particularly useful in isothermal transcription based amplification processes for the amplification of nucleic acid. The use of the RNA polymerases in isothermal transcription based amplification methods is therefore also part of the present invention.

Transcription based amplification techniques involve the transcription of multiple RNA copies from a template comprising a promoter recognized by an RNA polymerase. With these methods multiple RNA copies are transcribed from a DNA template that comprises a functional promoter recognized by the RNA polymerase. Said copies are used as a target again from which a new amount of the DNA template is obtained etc. Such methods have been described by Gingeras et al. in WO88/10315 and Burg et al. in WO89/1050. Isothermal transcription based amplification techniques have been described by Davey et al. in EP 323822 (relating to the NASBA method), by Gingeras et al. in EP 373960 and by Kacian et al. in EP 408295. Transcription based amplification reactions may also be performed with thermostable enzymes. Transcription based amplifications are usually carried out at a temperature around 37 to 41 Celsius. These thermostable enzymes allow the reaction to be carried out at more elevated temperatures (>41 C.). Such a thermostable method is described in EP 682121 filed in the name of Toyo Boseki K K.

The methods as described in EP 323822, EP 373960 and EP 408295 are isothermal continuous methods. With these methods four enzyme activities are required to achieve amplification: an RNA dependent DNA polymerase activity, an DNA dependent DNA polymerase activity, an RNase (H) activity and an RNA polymerase activity. Some of these activities can be combined in one enzyme, so usually only 2 or 3 enzymes are necessary. Enzymes having RNA dependent DNA polymerase activities are enzymes that synthesize DNA from an RNA template. A DNA dependent DNA polymerase thus synthesizes DNA from a DNA template. In transcription based amplification reactions a reverse transcriptase such as AMV (Avian Myoblastosis Virus) or MMLV (Moloney Murine Leukemia Virus) reverse transcriptase may be used for these activities. Such enzymes have both RNA- and DNA dependent DNA polymerase activity but also an inherent RNase H activity. In addition an RNase H may be added to the reaction mixture of a transcription based amplification reaction, such as E. coli RNase H.

The RNA polymerase that is commonly used with transcription based amplification methods is 7 RNA polymerase. Thus the promoter that is incorporated in the template used for transcribing multiple copies of RNA would than be the T7-promoter. Usually the template comprising the promoter has to be created starting from the nucleic acid comprising the target sequence. Said nucleic acid may be present in the starting material that is used as input for the amplification reaction. The nucleic acid present in the starting material will usually contain the target sequence as a part of a much longer sequence. Additional nucleic acid sequences may be present on both the 3'- and the 5'-end of the target sequence. The amplification reaction can be started by bringing together this nucleic acid from the starting material, the appropriate enzymes that together provide the above mentioned activities and at least one, but usually two, oligonucleotide(s). At least one of these oligonucleotides should comprise the sequence of the promoter.

Transcription based amplification methods are particularly useful if the input material is single stranded RNA, although single or double stranded DNA can likewise be used as input material. When a transcription based amplification method is practiced on a sample with single stranded RNA (of the "plus" sense) with additional sequences on both the 3'-end and the 5' end of the target sequence a pair of oligonucleotides that is conveniently used with the methods as described in the prior art would consist of:

A first oligonucleotide (usually referred to a "promoter-oligonucleotide") that is capable of hybridizing to the 3'-end of the target sequence, which oligonucleotide has the sequence of a promoter (preferably the T7 promoter) attached to its 5' end (the hybridizing part of this oligonucleotide has the opposite polarity as the plus RNA used as input material).

A second oligonucleotide ("primer") which comprises the 3' end of the target sequence (this oligonucleotide has the same polarity as the plus RNA).

When such a pair of oligonucleotides, together with all enzymes having the appropriate activities, and a sufficient supply of the necessary ribonucleotides and deoxy-ribonucleotides are put together in one reaction mixture and are kept under the appropriate conditions (that is, under the appropriate buffer conditions and at the appropriate temperature) for a sufficient period of time an isothermal continuous amplification reaction will take place.

The RNA polymerases according to the invention may also be used in conjunction with other nucleic acid amplification processes. With the Polymerase Chain reaction sometimes primers are used that in which a promoter sequence for a bacteriophage RNA polymerase, especially the promoter sequence for the T7 RNA polymerase, has been incorporated. This enables the transcription of the RNA form the DNA product of the PCR reaction. Again the RNA polymerases according to the invention may likewise be applied.

Thus, an enzyme mixture for use in an isothermal transcription based amplification reaction comprising, an RNA polymerase as provided by the present invention, an enzyme having reverse transcriptase activity and an enzyme having RNase H activity, is likewise part of the present invention.

Figure 1:
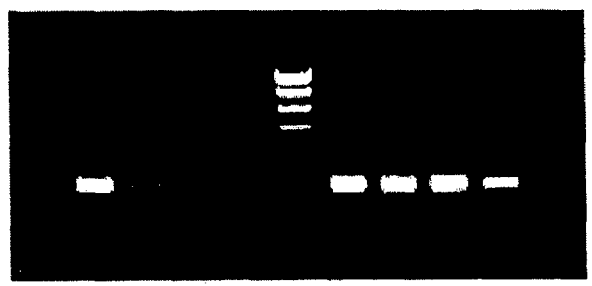
FIG. 1: Results of transcription assay for the wild type and the quadruple mutant at various temperatures.

The invention is further exemplified by the following examples:

EXAMPLE 1

Introduction of the Mutation(s) into His-Tagged T7 RNAP Gene on the Expression Plasmid.

Substitution of mutations was carried out by means of site-directed mutagenesis using QuickChange site-directed mutagenesis kit (STRATAGENE). The whole procedure was performed is according to the manufacture's protocol enclosed with the kit. The oligo primers used for introduction of the serine to proline at amino acid position 633 of T7 RNA polymerase mutation are as follows.

```
A: 5'-GTG-TGA-CTA-AGC-GTC-CGG-TCA-TGA-CGC-TGG-3'
(SEQ ID NO: 1)

B: 5'-CCA-GCG-TCA-TGA-CCG-GAC-GCT-TAG-TCA-CAC-3'
(SEQ ID NO: 2)
```

Oligonucleotide B is complementary to oligonucleotide A. The underlined sequence indicates the restriction site for Mspl, which is used for screening of mutant clones to contain the oligonucleotide sequences with the T→C mutation at position 1897 of the T7 RNA polymerase nucleotide sequence.

The primers used to introduce the other mutations are indicated below:

```
A: 5'-GTT TAC GCT GTC CCA ATG TTC ACC CCG CAA-3'
(SEQ ID NO: 3)

B: 5'-TTG CGG GTT GTT CAT TGG CAC AGC GTA AAC-3'
(SEQ ID NO: 4)

A: 5'-TTC TAC GAC CAG ATC GCT GAC CAG TTG CAC-3'
(SEQ ID NO: 5)

B: 5'-GTG CAA CTG GTC AGC GAT CTG GTC GTA GAA-3'
(SEQ ID NO: 6)

A: 5'-TCT TAG AGT CGG ACT ACG CGT TCG CGT AAC-3'
(SEQ ID NO: 7)

B: 5'-GTT ACG CGA ACG CGT AGT CCG ACT CTA AGA-3'
(SEQ ID NO: 8)
```

PCR reaction mixture and conditions were as follows.

| | |
|---|---|
| 10x Pfu buffer | 5 μl |
| Oligonucleotide A (100 ng/μl) | 1.25 μl |
| Oligo B | 1.25 μl |
| 2 mM dNTPs | 1.25 μl |
| plasmid template* | 1 μl |
| H2O | 41 μl |
| total | 50 μl |

The plasmid template contains the complete T7 RNA polymerase wild type gene sequence as published in the databases (Dunn, J. J. and Studier, F. W. (1983) Complete nucleotide sequence of bacteriophage T7 DNA and the locations of T7 genetic elements *J. Mol. Biol.* 166 (4), 477-535) fused to a histidine tag for simple purification in later procedures. T7 RNA polymerase gene was cloned by PCR using T7 DNA (Sigma D4931) as a template. The PCR-amplified T7 RNA polymerase DNA was then cloned into appropriate restriction site of pUC18(tag) plasmid which was made in advance by inserting tag sequence into the multiple cloning site (MCS) of pUC18. After making sure the DNA sequence of T7 RNAP gene was inserted by sequencing, the Tag-T7 RNA polymerase fusion gene was subcloned into appropriate site of pKK223-3 expression plasmid (Pharmacia Biotech 27-4935-01) to make Tag-T7RNAP/pKK223-3.

The PCR reaction was performed with the following temperature cycling protocol:

| | |
|---|---|
| 95° C. | 30 sec |
| 55° C. | 1 min |
| 68° C. | 14 min/18 cycles |

After the PCR reaction, 10 units of Dpnl restriction enzyme was added and incubated at 37° C. for 1 hr. One μl of Dpnl-treated DNA was then used for transformation of *E. coli* JM109. Finally, the mutant T7 RNA polymerase clone was isolated by screening the plasmid DNA using the Mspl restriction enzyme.

EXAMPLE 2

Mutant T7 RNA polymerase gene(s) containing plural mutations (amino acid substitutions) was constructed by substituting the restriction fragment containing a mutation for the same fragment of the mutant gene which contains other mutation(s). The restriction sites used for substitution were as follows:

```
                                                    T7RNAP gene
-Nucleotide No.      695           1675          2445
----BstXI----(T1288C)----HpaI----(T1897C)---KpnI----//
                                  2575      2650
              //----(T2545A)---MunI----(T2639A)----(HindIII)
```

EXAMPLE 3

In Vitro Transcription Assay

Reaction mixture for the in vitro transcription assay is as follows:

| | |
|---|---|
| 10 × T7 RNAP buffer | 5 μl |
| rNTP(each 25 mM) | 0.8 μl |
| 0.1% BSA | 5 μl |
| Rnase inhibitor (40 units/μl) | 0.5 μl |
| Template plasmid (0.5 μg/μl) | 1 μl |
| T7RNAP | 25 units |
| H2O/total | 50 μl |

Incubate at each temperature for 60 minutes

Apply 3 μl of above reaction mixture on 0.7% agarose gel.

Results are depicted in FIG. 1.

EXAMPLE 4

Comparison of Specific Activity of W.T. and Quadruple Mutant (F880Y+F849I+S633P+S430P)

The following protocol is used to determine the enzymatic transcription activity of T7 RNA polymerase.

1. Prepare the following reaction mixture

|  | (For 1 assay) | (For 10 assays) |
| --- | --- | --- |
| 10xtranscription buffer (*2) | 5 μl | 50 μl |
| 100mM rNTP mix (25mM each rNTP) | 0.8 μl | 8 μl |
| T7 DNA (Sigma D4931)(0.5 μg/μl) | 2 μl | 20 μl |
| BSA(1 mg/ml) | 2.5 μl | 25 μl |
| H20 | 34.2 μl | 342 μl |
| [3H] rUTP (NEN: NET-287) | 0.5 μl | 5 μl |
| total | 45 μl | 450 μl |

2. Dispense 45 μl of above reaction mixture to 2 ml eppendorf tubes
3. Incubate the mixture at 37° C. for 3 minutes (pre-incubation).
4. Add 5 μl of enzyme solution (*1) to be assayed, and mix well briefly.
5. Incubate at 37° C. for 10 minutes
6. Add 1.5 ml of 3.6% PCA solution (3.6% Perchloric acid, 0.1M $Na_4P_2O_7$) to stop the reaction, and incubate on ice for 10 minutes.
7. Filtrate and measure [3H] according to standard methods.

In this assay, transcription activity is calculated by using the following formula:

Activity(units/μl)=[$cpm$(Sample)−$cpm$(Blank)]×24/$cpm$(Total)

(1 unit is defined as a activity to catalyzes the incorporation of 1 nmole of labelled nucleotidetriphosphate into acid-insoluble material in 60 minutes)

| (*1) if necessary, dilute the enzyme solution to 0.5-4 units/μl with dilution buffer | |
| --- | --- |
| Dilution buffer: | 20 mM $KPO_4$ (pH 7.5) |
|  | 100 mM NaCl |
|  | 0.1 mM EDTA |
|  | 1 mM DTT |
|  | 50% (V/V) Glycerol |
| (*2) 10 × transcription buffer | 400 mM Tris-HCl (pH 8.0) |
|  | 200 mM $MgCl_2$ |
|  | 50 mM DTT |

Results are depicted in Table 2:

TABLE 2

|  | Specific activity (units/μg protein) | |
| --- | --- | --- |
| Reaction Temperature | W.T. | Q-mutant |
| 37 | 22.0 | 29.9 |
| 40 | 26.9 | 35.9 |
| 45 | 32.2 | 49.6 |
| 50 | 4.8 | 56.8 |
| 55 | 1.6 | 8.8 |
| 60 | 0.0 | 3.3 |
| 65 | 0.0 | 0.9 |

EXAMPLE 5

In this example the half life $T_{1/2}$, of different T7 RNA polymerases is determined using the following protocol:

1. Prepare the following reaction mixture

| (For I assay) | |
| --- | --- |
| 10x transcription buffer | 10 μl |
| 0.5 M KCl | 14 μl |
| BSA (1 mg/ml) | 10 μl |
| H2O | 56 μl |
| total | 90 μl |

(transcription buffer: 400 mM tris, pH=8.0, 200 mM $MgCl_2$ and 50 mM DTT.

2. Add 10 μl of enzyme solution to be assayed, and mix well.
3. Incubate at the appropriate temperature
4. Take 5 μl at every 5 or 10 minutes, and immediately transfer to reaction mixture of transcription activity assay (see example 3) and measure the (residual) activity.
5. Plot ln[[cpm(t=T)−cpm(Blank)]/[cpm(t=0)−cpm(Blank)]] against T(incubation time).
6. T½ (min) is deduced as e(=2.718)/slope.

The results of a comparison between the wild-type T7 RNA polymerase and the mutants

TABLE 1

$T_{1/2}$ compared between T7 wild-type and T7 mutants

|  |  | T ½ (min) | | |
| --- | --- | --- | --- | --- |
|  | SA (units/μg | At 50.0 | At 48.0 | At 46.0 |
| Mutation | protein | Test 1 | Test 1 | Test 2 | Test 1 |
| WT | 24.9 |  | 1.9 | 2.1 | 16.6 |
| S430P |  |  |  | 6.8 |  |
| S633P | 38.7 |  | 9.3 | 9.0 | 58.3 |
| F849I | 39.2 |  | 9.8 |  | 53.3 |
| F880Y | 32.4 |  | 8.4 |  | 42.7 |
| S633P + F849I | 31.7 | 6.7 | 46.0 |  |  |
| S633P + F880Y | 35.3 | 4.5 | 49.3 |  |  |
| F849I + F880Y | 33.8 | 5.9 | 37.8 |  |  |
| S633P + F849I + F880Y | 35.0 | 28.0 | 58.0 |  |  |
|  |  | 84.5 |  |  |  |

EXAMPLE 6

Establishment of Large Scale Production System of T7 RNAP Enzyme.

To obtain large quantity of enzyme, conditions for cultivating E. coli and purification of T7 RNAP enzyme were examined. Conditions finally determined were as follows. For purification conditions, reference is made to a publication by Studier (P.N.A.S., USA, 81, 2035-2039, 1984.

6.1: Procedure for Cultivating E. Coli Harboring T7 RNAP Expression Plasmid.

1. Inoculate single colony E. coli BL21 harboring T7 RNAP expression plasmid into 2 ml of LB medium and cultivate at 30° C. for 16 hours (seed seed culture).
2. Inoculate 1 ml of seed culture into 100 ml of LB medium and cultivate at 30° C. for 16 hours (seed culture).

3. Inoculate 100 ml of seed culture into 6 L of TB medium and cultivate at 37° C. for 10-12 hr (main culture). (All medium used contains 50 µg of ampicillin per ml.)

| LB medium: | Tripton peptone (Difco) | 10 g |
| | Yeast Extract (Difco) | 5 g |
| | NaCl | 10 g/L |
| | Adjust pH 7.5 with NaOH | |
| TB medium: | Tripton peptone (Difco) | 12 g |
| | Yeast Extract(Difco) | 24 g |
| | $KH_2PO_4$ | 2.31 g |
| | $K_2HPO_4$ | 12.5 g |
| | Glycerol | 4 ml/L |

The results are given in Table 2:

TABLE 2

| Cultivation time (hours) | OD 660 | PH |
| --- | --- | --- |
| 0 | 0.75 | 6.96 |
| 2 | 2.45 | 6.81 |
| 4 | 5.75 | 6.7 |
| 6 | 7.35 | 6.44 |
| 8 | 12.3 | 6.83 |
| 10 | 16.6 | 7.47 |
| 12 | 19.15 | 8.05 |
| 14 | 19.5 | 8.35 |
| 16 | 18.75 | 8.49 |
| 18 | 17.2 | 8.54 |
| 20 | 16.3 | 8.57 |
| 22 | 15.05 | 8.56 |

Using these conditions, 120 g of *E. coli* (wet weight) are usually obtained.

6.2 Procedure for Purification of T7 RNAP.

1. 100 g of *E. coli* cells was suspended in 500 ml of buffer A and disrupted by Frenchpress. This lysate was then centrifuged and supernatant (crude extract) was obtained.

2. To the crude extract, 16,9 ml of 5% Polyethylenimine (PEI) solution was added to precipitate nucleic acids. Supernatant was obtained by centrifugation.

3. To the supernatant after PEI treatment, ammonium sulfate was added to final 45% saturation. The mixture was stirred at 45° C. for 30 min to allow precipitation. The ammonium sulfate precipitate was collected by centrifugation, dissolved in 200 ml of buffer B (+50 mM NaCl), and then dialyzed against the same buffer.

4. The enzyme solution was loaded on 100 ml column of Affi-Gel blue (Bio-Rad). The column was washed with buffer B (+100 mM NaCl), and the protein was eluted with buffer B (+2M NaCl). The peak fractions were pooled.

5. To the collected pool, ammoniumsulfate was added to final 45% saturation. The ammonium sulfate precipitate was then collected, dissolved in 200 ml of Buffer B (+25 mM NaCl), dialyzed against the same buffer, and loaded on 200 ml column of DEAE-cellulofine column. The column was washed with buffer B (+25 mM NaCl), and the protein was eluted with 1000 ml of gradient form 25 to 150 mM NaCl. The peak fractions were collected.

6. To the collected pool, ammoniumsulfate was added to final 45% saturation. The ammonium sulfate precipitate was then collected, dissolved in 30 ml storage buffer and dialyzed against the same buffer.

The resulting enzyme was finally filtrated and stored at −300° C.

| Buffer A: | | Buffer B: | | Storage buffer | |
| --- | --- | --- | --- | --- | --- |
| 50 mM | Tris-HCl (pH 8.0) | 20 mM | $KPO_4$ (PH 7.7) | 20 mM | $KPO_4$ (pH 7.7) |
| 1 M | NaCl | | NaCl | 100 mM | NaCl |
| 2 mM | EDTA | 1 mM | EDTA | 0.1 mM | EDTA |
| 1 mM | DTT | 1 mM | DTT | 1 mM | DTT |
| | | 5% | Glycerol | 50% | Glycerol |
| | | | | 0.01% | TritonX-100 |

Results are depicted in Table 3:

TABLE 3

Summary of purification:

| | Step | Vol. (ml) | Activity (Units/µl) | Total Activity (KU) | Protein Conc. (mg/ml) | Total protein (mg) | Speicifc activity (units/µg) |
| --- | --- | --- | --- | --- | --- | --- | --- |
| 1 | Crude Extract | 845 | ND | — | 24.6 | 20787 | — |
| 2 | After PEI | 869 | ND | — | 23.4 | 20124 | — |
| 3 | After salting out | 200 | 805.1 | 161012 | 36.5 | 7300 | 22.0 |
| 4 | After Affi-gel blue | 524 | 312.3 | 163619 | 5.2 | 2724 | 60.1 |
| 5 | After DEAE cellulo. | 220 | 354.3 | 77950 | 3.8 | 836 | 93.2 |
| 6 | After salting out and dialysis | 37 | 1865 | 69025 | 19.2 | 710 | 97.2 |

6.3 Quality Control Assays for Purified T7 RNAP

The purified enzyme was tested by the following Quality Control Assays and the in vitro transcription assay.

Functional Absence of Exonuclease Activity:

120 units of the purified enzyme was incubated with 10 μl of 3H-*E. coli* (NET-561) at 37° C. for 4 hours. The release of acid soluble DNA is less than 0.01% /units/hour Functional Absence of Endonuclease Activity:

60 units of the purified enzyme is incubated with 1 μg of phiX174 DNA at 37° C. for 4 hours. No visible change is detected in band pattern upon agarose gel electrophoresis.

Functional Absence of Rnase Activities:

200 units of the purified enzyme is incubated with 2 μg of 16S&24S ribosomal RNA (Boehringer) at 37° C. for 4 hours. No visible change is detected in band pattern upon agarose gel electrophoresis.

Performance of Transcription Reaction.

Each 30 units of the purified enzyme and a commercially available RNAP were used in the following in the vitro transcription assay described above.

Mixtures were incubated at both 37 and 48 degrees Celsius for 1 hour. The quantity of RNA produced by the purified enzyme at 48 degrees Celsius was almost the same as the quantity of RNA produced by the commercially available enzyme ate 37 degrees.

The invention claimed is:

1. A T7 RNA polymerase comprising a mutation selected from the group consisting of S430P, F849I, and a combination thereof, wherein said T7 RNA polymerase has a phenotype as a result of said mutation of increased stability and polymerase activity as compared to a T7 RNA polymerase lacking said mutation, wherein said mutation positions are relative to the T7 RNA polymerase wild-type amino acid sequence of SEQ ID NO:10.

2. The T7 RNA polymerase according to claim 1, wherein said T7 RNA polymerase further comprises an S633P mutation.

3. The T7 RNA polymerase according to claim 1, characterized in that said T7 RNA polymerase comprises an S430P mutation and an F849I mutation.

4. The T7 RNA polymerase according to claim 1, wherein said T7 RNA polymerase further comprises an F880Y mutation.

5. The T7 RNA polymerase according to claim 2, further comprising an F880Y mutation.

6. A nucleic acid molecule encoding the T7 RNA polymerase according to claim 1.

7. An expression vector comprising the nucleic acid molecule according to claim 6 and suitable expression control sequences.

8. An isolated cell transformed with the expression vector according to claim 7, and capable of expressing said T7 RNA polymerase.

9. A method of amplifying a target nucleic acid in a sample in an isothermal transcription based nucleic acid amplification reaction, comprising contacting the sample with:

a) a primer pair comprising a first promoter-oligonucleotide and a second oligonucleotide for amplification of the target nucleic acid; and b) the T7 RNA polymerase of claim 1, under conditions whereby the isothermal transcription based nucleic acid amplification reaction can occur to amplify the target nucleic acid.

10. An enzyme mixture for use in an isothermal transcription based nucleic acid amplification reaction comprising:

a) the T7 RNA polymerase according to claim 1; and b) an enzyme having reverse transcriptase activity and optional RNase H activity.

11. The T7 RNA polymerase of claim 5, comprising an S430P mutation, an S633P mutation, an F849I mutation and an F880Y mutation.

12. A nucleic acid molecule encoding the T7 RNA polymerase according to claim 5.

13. An expression vector comprising the nucleic acid molecule according to claim 12 and suitable expression control sequences.

14. An isolated cell transformed with the expression vector according to claim 13, and capable of expressing the T7 RNA polymerase.

15. A method of amplifying a target nucleic acid in a sample in an isothermal transcription based nucleic acid amplification reaction, comprising contacting the sample with:

a) a primer pair comprising a first promoter-oligonucleotide and a second oligonucleotide for amplification of the target nucleic acid; and b) the T7 RNA polymerase of claim 5, under conditions whereby the isothermal transcription based nucleic acid amplification reaction can occur to amplify the target nucleic acid.

16. An enzyme mixture for use in an isothermal transcription based amplification reaction comprising:
    a) the T7 RNA polymerase according to claim 5; and
    b) an enzyme having reverse transcriptase activity and optional RNase H activity.

17. A T7 RNA polymerase comprising an S633P mutation and an F880Y mutation, wherein said T7 RNA polymerase has a phenotype as a result of said mutations of increased stability and polymerase activity as compared to a T7 RNA polymerase lacking said mutation, wherein said mutation positions are relative to the T7 RNA polymerase wild-type amino acid sequence of SEQ ID NO:10.

18. A nucleic acid molecule encoding the T7 RNA polymerase according to claim 17.

19. An expression vector comprising the nucleic acid molecule according to claim 18 and suitable expression control sequences.

20. An isolated cell transformed with the expression vector according to claim 19, and capable of expressing said T7 RNA polymerase.

21. A method of amplifying a target nucleic acid in a sample in an isothermal transcription based nucleic acid amplification reaction, comprising contacting the sample with:
    a) a primer pair comprising a first promoter-oligonucleotide and a second oligonucleotide for amplification of the target nucleic acid; and
    b) the T7 RNA polymerase of claim 17, under conditions whereby the isothermal transcription based nucleic acid amplification reaction can occur to amplify the target nucleic acid.

22. An enzyme mixture for use in an isothermal transcription based amplification reaction comprising:
    a) the T7 RNA polymerase according to claim 17; and
    b) an enzyme having reverse transcriptase activity and optional RNase H activity.

* * * * *

UNITED STATES PATENT AND TRADEMARK OFFICE
CERTIFICATE OF CORRECTION

PATENT NO. : 7,507,567 B2  Page 1 of 1
APPLICATION NO. : 10/220908
DATED : March 24, 2009
INVENTOR(S) : Sugiyama et al.

It is certified that error appears in the above-identified patent and that said Letters Patent is hereby corrected as shown below:

On Title Page:
Item 73, Assignee: Please correct "bioMerieus B.V."
to read -- bioMerieux B.V. --

Title Page, After the title please add the following:
Item -- [60] Related Application Information
This application claims the benefit under 35 U.S.C. § 371 from PCT Application No. PCT/EP01/02327, filed March 1, 2001, which claims priority from European Application Serial No. 00200787.0, filed March 7, 2000, the disclosures of which are incorporated by reference herein in their entirety. --

Signed and Sealed this

Nineteenth Day of May, 2009

JOHN DOLL
*Acting Director of the United States Patent and Trademark Office*